United States Patent [19]

Nagatsu et al.

[11] 4,119,620

[45] Oct. 10, 1978

[54] NOVEL DIPEPTIDE DERIVATIVES, SALTS THEREOF, AND METHOD OF MEASURING ENZYME ACTIVITY

[75] Inventors: Toshiharu Nagatsu, Yokohama; Shumpei Sakakibara, Suita, both of Japan

[73] Assignee: Ajinomoto Co., Inc., Tokyo, Japan

[21] Appl. No.: 733,343

[22] Filed: Oct. 18, 1976

[30] Foreign Application Priority Data

Oct. 30, 1975 [JP] Japan ................................. 50/130809

[51] Int. Cl.$^2$ ......................... C07C 103/52; B41J 5/12
[52] U.S. Cl. ....................... 260/112.5 R; 195/103.5 R
[58] Field of Search ............... 260/112.5 R; 195/103.5

[56] References Cited

PUBLICATIONS

Pettit; Synthetic Peptides I, (1971) pp. 124–125.

*Primary Examiner*—Delbert R. Phillips
*Attorney, Agent, or Firm*—Cooper, Dunham, Clark, Griffin & Moran

[57] ABSTRACT

The activity of X-prolyl dipeptidyl-aminopeptidase against X-L-proline-Y wherein X is an amino acid residue and Y is p-nitroaniline, p-phenylazoaniline or 4-phenylazo-1-naphthylamine is used as a measure of human afflictions such as hepatobiliary diseases and carcinomas.

10 Claims, No Drawings

NOVEL DIPEPTIDE DERIVATIVES, SALTS THEREOF, AND METHOD OF MEASURING ENZYME ACTIVITY

This invention relates to novel dipeptide derivatives, salts thereof, and a method of measuring enzyme activity by using these compounds as substrates.

Many investigations have been made in order to clarify the relation between activities of enzymes present in animals including human beings and various diseases. Some correlation has been observed and enzyme activities have been used as diagnostic aids. For example, not only the activity of leucine aminopeptidase has been measured for distinguishing obstructive jaundice from parenchymal jaundice, but also the activities of glutamic-oxalacetic transaminase, glutamic transaminase and lactate dehydrogenase have been widely measured to diagnose hepatic diseases. However, these enzyme levels are usually elevated in patients as compared with healthy subjects, and thus diagonoses by such measurements are not highly reliable unless other clinical data are considered.

We have been making researches on enzymes in animals including human beings and activities thereof in order to establish more reliable, safe and simple diagnostic aids. We have first synthesized novel dipeptide derivatives having the structure of X-L-proline-Y (X; amino acid residue, Y; residue of p-nitroaniline, p-phenylazoaniline, or 4-phenylazo-1-naphthylamine) and salts thereof, and examined whether an enzyme capable of hydrolyzing these novel compounds exists in animals, or not. As a results, we have found a single enzyme named as X-prolyl dipeptidyl-aminopeptidase, which is one of the dipeptidyl-aminopeptidase. It hydrolyzes these dipeptide derivatives into X-L-proline and Y-H (namely, p-nitroaniline, p-phenylazoaniline, or 4-phenylazo-1-naphthylamine), in serum from various animal species including human beings, in human saliva and salivary glands, in various connective tissues such as bovine or human dental pulp, dental follicles, gingiva, and rat granuloma. We have measured the X-prolyl dipeptidyl-aminopeptidase activity in normal human sera using these dipeptide derivatives or salts thereof as substrates, and have found that the enzyme levels are almost the same in normal subjects although there are slight but significant differences between younger males and younger females and between older females and younger females. However, the enzyme levels in human sera were found to be remarkably elevated in patients with hepatobiliary diseases (for example, acute and chronic hepatitis, liver cirrhosis) and with essential hypertension, and suprisingly decreased highly significantly in patients with malignant tumors such as solid cancers (for example, gastric cancer, pancreatic cancer, pulmonary cancer), and blood cancers and sarcomas (for example, leukemia, lymphosarcoma, Hodgkin's disease). Thus, we have confirmed that the activity measurement of the X-prolyl dipeptidyl-aminopeptidase, especially in human serum by using the novel dipeptide derivatives or salts thereof as substrates is a very useful diagnostic aid for diseases, especially for malignant tumors.

Furthermore, we have confirmed that the present novel dipeptide derivatives and salts thereof are safe compounds which are not carcinogenic, and that these compounds fulfill various characteristics required of substrates such as; easy assay of substrate hydrolyzed by enzyme, stability, and linear relation between amount of hydrolyzed substrate and of enzyme, and between amount of hydrolyzed substrate and incubation time.

The N-terminal amino acid residue (X) of the present novel dipeptide derivatives, X-L-proline-Y, includes any amino acid residues, because the enzyme is specific for the second amino acid residue, L-proline residue, but not for the N-terminal amino acid residue. The N-terminal amino acid is usually selected from $\alpha$-amino acids having up to 15 carbon atoms and existing in protein, for example, neutral amino acids such as glycine, alanine, valine, leucine, serine, threonine, phenylalanine, tyrosine, and tryptophane; acidic amino acids such as glutamic acid, and aspartic acid; and basic amino acids such as lysine and arginine. These amino acids are able to have any stereochemical configuration; L, D, and DL, if they have an assymetric carbon, however usually they have the L-form. Furthermore, these dipeptide derivatives are used as substrates not only in the free form, but also in the form of salts with acids which do not inhibit enzyme activity, such as p-toluenesulfonic acid, hydrochloric acid and hydrobromic acid. Since the salts are more stable than the free base, the salts are usually preferred as substrates.

The portion Y of X-L-proline-Y is chosen from the group consisting of the residues of p-nitroaniline, p-phenylazoaniline, and 4-phenylazo-1-naphthyl-amine. Among them, the residue of p-nitroaniline is most successfully employed because the dipeptide derivative bearing the same has the highest solubility in water, is most stable and is more easily synthesized.

The enzyme activity toward the novel dipeptide derivatives, X-L-proline-Y, is different depending on the kind of the N-terminal amino acid residue (X). The dipeptide derivatives bearing neutral or basic amino acid residues as the portion X are most highly hydrolyzed by the enzyme and those bearing acidic amino acid residues are the lowest. Thus, the dipeptide derivatives bearing neutral or basic amino acid residues or the salts with acids such as p-toluenesulfonic acid are suitable as substrates in this point, but the basic amino acid derivatives are hygroscopic. On the other hand, the dipeptide derivatives bearing glycine residue has the highest rate of hydrolysis at its optimum pH 8.7 among various dipeptide derivatives, X-L-proline-Y, and is fairly stable in the dark and easily solubilized in water. Furthermore, the glycine derivative, especially its salts with acids such as hydrochloric acid and p-toluenesulfonic acid is not hygroscopic in contrast with the basic amino acid derivatives, and is convenient in the assay operation. In over all respects, glycyl-L-proline p-nitroanilide or its salts, especially the p-toluenesulfonate (the tosylate) are the best substrates.

The present novel dipeptides having the structure of X-L-proline-Y are easily synthesized by methods known in peptide chemistry. They may be obtained by eliminating the masking group from N-masked-X-L-proline-Y which may be synthesized by coupling L-proline-Y with N-masked-amino acid corresponding to the N-masked-X portion by the action of condensing agents such as carbodiimide derivatives, or by the active ester method and the like. The masking group suitable for the N-terminal amino acid may be chosen from known groups such as benzyloxycarbonyl, t-butyloxycarbonyl, and t-amyloxycaybonyl.

If the amino acids employed have side functional groups, they may be employed after the functional groups are masked. For example, in case of acidic amino acids, they are used after side carboxylic groups are converted to ester groups such as benzyl ester group. Arginine is used after the guanidino group is masked with usual masking groups such as tosyl, nitro, p-nitrobenzylcarbonyl, and 2-(isopropyloxycarbonyl) 3, 4, 5, 6-tetrachlorobenzoyl, especially the former two groups, while the N$^\epsilon$-amino group of lysine is usually masked with known amino-masking groups, preferably with the same masking group as selected for the N$^\alpha$-amino group.

The masking group of N-masked-X-L-proline-Y thus obtained is then eliminated by any known method depending on the particular N-masking group, and the masking group for side functional groups, if any. It is important to eliminate only the masking groups without affecting other members in this elimination reaction.

It is also possible to synthesize the desired dipeptide derivatives by first coupling the N-masked-X-L-proline with Y-H and then eliminating the masking group from the formed N-masked-X-L-proline-Y.

If the salts of dipeptide derivatives with acids are desired, they are readily prepared by contacting the free base with the acids in a medium such as water, ethanol and the like. The salts are also directly obtained from the N-masked derivatives by contacting the same with acids, if the masking groups are t-butyloxycarbonyl and the like which can be eliminated by the action of acids.

Among various salts with acids, the tosylate is most preferred because it forms rigid crystals containing few of the impurities which may have been present in the mother liquor, and thus which can be obtained in a high purity by simple recrystallization.

The enzyme activity is measured without difficulty by using the dipeptide derivatives or salts thereof as substrates. An aqueous solution of X-L-proline-Y or salt thereof having a suitable concentration is first prepared. Since it requires a fairly long time to dissolve the substrate in water, it is preferred to use suitable substances capable of increasing the dissolution rate such as non-ionic detergents, acids and alcohols, or to use the substrate in the porous form which may be prepared by freeze-drying or the like. The porous substrate is most convenient for routine use for assay of the enzyme. The optimum pH of the substrate solution varies depending on the kind of substrate employed, but is easily determined by experiments. The optimum pH is usually in the range of from 6 to 9, preferably of from 7.5 to 8.9. The substates are spontaneously hydrolyzed at above pH 9.5, but the substrate solutions, especially glycyl-L-proline p-nitroanilide solution is stable at the above-mentioned optimum pH, and can be stored at 4° C. for more than a week without appreciable degradation.

The enzyme activity is measured by contacting the substrate with the X-prolyl dipeptidylaminopeptidase or a sample containing the same in an aqueous medium, preferably in a buffer solution such as trismaleate buffer glycine-NaOH buffer and amidiol buffer, at 30° to 45° C. for a certain period, deactivating the enzyme in an usual manner, and then assaying the liberated Y-H. The incubation time is determined according to the amounts of substrate and enzyme. Even if crude enzyme such as human serum is used as enzyme source, the activity is accuretely measured because the substrate is not substantially hydrolyzed by other enzymes which are present in the crude enzyme.

The amount of liberated Y-H is easily assayed by measuring the absorbance of the enzymic reaction mixture directly at the wave length suitable for the specific Y-H, namely at 385 nm for p-nitroaniline, 493 nm for p-phenylazoaniline, and 532 nm for 4-phenylazo-1-naphthylamine. This direct photometric method is very simple, convienient, and accurate, and thus suitable for routine assay of the enzyme activity.

When the Y-H is p-nitroaniline, the enzyme activity can also be assayed by diazotization of p-nitroaniline formed with excess sodium nitrite in acidic medium. In this assay, the amount of p-nitroaniline formed can be calculated by assaying the unreacted sodium nitrite, but it is usually determined by so-called azo-coupling method; decomposing the unreacted sodium nitrite with sulfamic acid, ammonium sulfamate, urea, and the like, reacting the p-nitrophenyldiazonium formed with a coupling component such as N-(1-naphthyl) ethylenediamine, and then measuring the absorbance of the formed azo compound at the wave length suitable for such azo compound. This indirect assay method is more complicated than the former direct photometric method, but is more sensitive. It is also highly effective, when the available amount of enzyme is very small.

The following Examples illustrate the invention in more detail.

EXAMPLE 1

(N-Benzyloxycarbonyl-L-proline p-nitroanilide)

Phosphoryl trichloride (50.6 g, 0.33 mole) was stirred slowly into a solution of N-benzyloxycarbonyl-L-proline (74.8 g, 0.3 mole) and p-nitroaniline (41.4 g, 0.3 mole) in tetrahydrofuran (400 ml) at −10° C. Triethylamine (92.4 ml, 0.66 mole) was added dropwise into the mixture, the inside temperature being kept at −15° C. After being adjusted to pH 7 with triethylamine, the reaction mixture was allowed to come to room temperature, and was stirred for 3 hours.

The solvent was exchanged with ethyl acetate (1.2 l), the solution was washed successively with water (400 ml), 1N-hydrochloric acid (300 ml × 5), water (400 ml), 5% sodium hydrogencarbonate solution (300 ml × 3) and saturated sodium chloride solution (300 ml), and dried over magnesium sulfate. The dried solution was concentrated under reduced pressure, the residue was crystallized by adding ethyl ether and the product was recrystallized from a mixture of ethyl acetate (300 ml) and methanol (50 ml).

Yield: 56 g
m.p.: 159°–161° C.
$[\alpha]_D^{25}$: −107.6° (C=1.0, methanol)

| Elemental Analysis | C | H | N% |
|---|---|---|---|
| Calcd. for $C_{19}H_{19}O_5N_3$: | 61.77 | 5.19 | 11.38 |
| Found: | 62.07 | 5.20 | 11.62 |

EXAMPLE 2

(L-Proline p-nitroanilide hydrobromide)

N-Benzyloxycarbonyl-L-proline p-nitroanilide (55.4 g, 0.15 mole) was dissolved in 26% anhydrous hydrogen bromide solution in acetic acid (200 ml) at 0° C., and the mixture was stirred for 2 hours at room temperature. The solution was stirred into dry ethyl ether (2 liter) to crystallize out the product, which was separated by decantation, washed with ethyl ether, and dried.

Yield 47 g.

The crude product was used in the following Examples without further purification. An analytical sample was prepared by recrystallization from methanol-ethanol.

m.p.: 225°–226° C.

$[\alpha]_D^{22}$: −35.6° (C=1.0, CH$_3$OH)

| Elemental Analysis | C | H | N% |
|---|---|---|---|
| Calcd. for C$_{11}$H$_{14}$O$_3$N$_3$Br: | 41.79 | 4.46 | 13.29 |
| Found: | 41.75 | 4.34 | 13.30 |

EXAMPLE 3

(N-Benzyloxycarbonyl-glycyl-L-proline p-nitroanilide)

N-Benzyloxycarbonyl-glycine ester of hydroxysuccinimide (48 g, 0.16 mole) was stirred into a cooled mixture of L-proline p-nitroanilide hydrobromide (47 g, 0.15 mole) triethylamine (22 ml) and N-hydroxybenztriazole (1 g) in dimethylformamide (100 ml). The whole mixture was stirred at 0° C. for 1 hour, the pH of the solution being kept at 8 with triethyl amine during the period, and then the stirring was continued for additional 19 hours at room temperature.

The solvent was removed by evaporation under reduced pressure, water (350 ml) was added to the residue, and the product was extracted twice with ethyl acetate (500 ml, 200 ml). The extracts were combined, washed successively with water (200 ml), 1N-hydrochloric acid (200 ml × 2), water (200 ml) and 5% sodium hydrogen carbonate solution (200 ml × 4) and water (200 ml), and dried over magnesium sulfate.

Yield 67 g.

Homogeneity of this material was confirmed by thin layer chromatography on silica gel using a mixture of chloroform, methanol and acetic acid (95:5:3, V/V/V) as developing solvent.

EXAMPLE 4

(Glycyl-L-proline p-nitroanilide)

N-Benzyloxycarbonyl-glycyl-L-proline p-nitroanilide (61 g) was reacted with 26% anhydrous hydrogen bromide solution in acetic acid (250 ml) and the reaction mixture was worked up as in Example 2. To produce, glycyl-L-proline p-nitroanilide hydrobromide was obtained.

Yield 59 g.

The hydrobromide (20 g) was suspended in 1M sodium carbonate solution (100 ml), and the suspension was extracted with chloroform (100 ml each) eight times after being saturated with sodium chloride. The extracts were combined, washed with saturated sodium chloride solution (100 ml), and dried over magnesium sulfate. The dried solution was concentrated, and the residue was crystallized from a mixture of ethyl acetate and ethyl ether.

Yield: 12.7 g m.p.: 118°–120° C.

$[\alpha]_D^{21}$: −115.8° (C=1.0, methanol)

$\epsilon_{max}^{315}$: 11600 (0.1N hydrochloric acid)

EXAMPLE 5

(Glycyl-L-proline p-nitroanilide tosylate)

Glycyl-L-proline p-nitroanilide (584 mg) was neutralized with an ethanol solution of p-toluenesulfonic acid monohydrate (380 mg in 10 ml). The product was crystallized out by keeping the solution in a refrigerator. The crude product was recrystallized from methanol-ethyl ether.

Yield: 312 mg m.p.: 223°–225° C. (decomp.)

$[\alpha]_D^{30}$: −81.0° (C=1.0, methanol)

| Elemental Analysis | C | H | N% |
|---|---|---|---|
| Calcd. for C$_{20}$H$_{24}$O$_7$N$_4$S: | 51.72 | 5.21 | 12.06 |
| Found: | 51.82 | 5.19 | 12.24 |

EXAMPLE 6

(t-Butyloxycarbonyl-L-alanyl-L-proline p-nitroanilide)

t-Butyloxycarbonyl-L-alanine (5.7 g, 0.03 mole) and L-proline p-nitroanilide hydrobromide (9.5 g, 0.03 mole) were dissolved in chloroform (40 ml) together with triethylamine (4.2 ml, 0.03 mole), and a solution of N, N'-dicyclohexylcarbodiimide (6.2 g, 0.03 mole) in chloroform (5 ml) was added into the solution at 0° C.

The mixture was stirred for 44 hours at room temperature and stirring was continued for additional 2 hours after adding few drops of acetic acid. The precipitated materials were removed by filtration, the filtrate was concentrated under reduced pressure.

The residue was suspended in water, and the product was extracted with ethyl acetate. The extract was washed successively with 1N-hydrochloric acid, water, 5% sodium hydrogen carbonate solution, water and saturated sodium chloride solution, and dried over magnesium sulfate. The dried solution was concentrated to a residue, which was dissolved in ethyl ether. Some insoluble materials were removed by filtration, the filtrate was concentrated, and the residue was solidified by the trituration with n-hexane.

Yield 12.9 g

This material showed a single spot on thin-layer chromatography.

EXAMPLE 7

(L-Alanyl-L-proline p-nitroanilide hydrochloride)

A solution of t-butyloxycarbonyl-L-alanyl-L-proline p-nitroanilide (12.9 g) in dioxane (20 ml) was treated with 6N solution of anhydrous hydrogen chloride in dioxane (45 ml) for 55 minutes at room temperature. The reaction mixture was concentrated under reduced pressure, and the residue was triturated with ethyl ether to form a solid, which was crystallized from ethanol.

Yield: 6.4 g m.p.: 130°–140° C. (decomp.)

$[\alpha]_D^{30}$: −103.4° (C=1.0, methanol)

| Elemental Analysis | C | H | N% |
|---|---|---|---|
| Calcd for C$_{14}$H$_{19}$O$_4$N$_4$Cl . 5/4H$_2$O: | 46.03 | 5.93 | 15.34 |
| Found: | 46.12 | 6.09 | 15.50 |

EXAMPLE 8

(t-Butyloxycarbonyl-β-benzyl-L-aspartyl-L-proline p-nitroanilide)

t-Butyloxycarbonyl-β-benzyl-L-aspartic acid (9.7 g, 0.03 mole) and L-proline p-nitroanilide hydrobromide (9.5 g, 0.03 mole) were coupled with each other as in Example 6. The crude product was chromatographed on a column of silica gel (3.6 cm × 19 cm), chloroform-ethyl acetate (5:1, v/v) being used as developing solvent. Fractions containing the main band were combined and concentrated to obtain an amorphous solid.

Yield 10.3 g.

This material was confirmed to be homogeneous by thin-layer chromatography.

EXAMPLE 9

(L-Aspartyl-L-proline p-nitroanilide)

t-Butyloxycarbonyl-β-benzyl-L-aspartyl-L-proline p-nitroanilide (10.3 g) was mixed well with anisole (8 ml), and the solution was treated with anhydrous hydrogen fluoride (about 50 ml) for 1 hour at 0° C. The hydrogen fluoride was distilled out, and the product was precipitated by adding ethyl ether. The precipitates were washed twice with ethyl ether, separated by decantation, and dried.

The crude product was dissolved in 0.1 M acetic acid, and the solution was washed well with ethyl ether, and passed through a column of a strong-base anion-exchange resin (Amberlite IR-400, acetate form, 200 ml), which was washed with 0.1 M acetic acid. The elute and washings were combined and concentrated under reduced pressure. The residue was crystallized from a small amount of water.

Yield: 5.2 g
m.p.: 144°–145° C. (decomp.)
$[\alpha]_D^{32}$: −100.3° (C=1.0, 1N-HCl)
$\epsilon_{max}^{315}$: 12170 (0.1N-HCl)

| Elemental Analysis | C | H | N% |
|---|---|---|---|
| Calcd. for $C_{15}H_{18}O_6N_4 \cdot 3/2H_2O$: | 47.74 | 5.61 | 14.85 |
| Found: | 48.03 | 5.63 | 14.16 |

EXAMPLE 10

(t-Butyloxycarbonyl-γ-benzyl-L-glutamyl-L-proline p-nitroanilide)

L-Proline p-nitroanilide hydrobromide (9.5 g, 0.03 mole) and t-butyloxycarbonyl-γ-benzyl-L-glutamic acid, which was liberated from the dicyclohexylamine salt (17.1 g, 0.03 mole) were coupled by N, N'-dicyclohyxylcarbodiimide as in Example 6. The crude product was purified by column chromatography to give an amorphous solid.

Yield 12.7 g.

The solid was confirmed as homogeneous by thin-layer chromatography.

EXAMPLE 11

(L-Glutamyl-L-proline p-nitroanilide)

t-Butyloxycarbonyl-γ-benzyl-L-glutamyl-L-proline p-nitroanilide (10 g, 0.018 mole) was treated with hydrogen fluoride (about 50 ml) and the reaction mixture was worked up as in Example 9. The final product was obtained as crystals.

Yield: 4.7 g
m.p.: 117°–126° C. (decomp.)
$[\alpha]_D^{25}$: −82.8° (C=1.0, water)

| Elemental Analysis | C | H | N% |
|---|---|---|---|
| Calcd. for $C_{16}H_{20}O_6N_4 \cdot 5/4H_2O$: | 49.66 | 5.87 | 14.48 |
| Found: | 49.73 | 5.91 | 14.54 |

EXAMPLE 12

($N^\alpha$, $N^\epsilon$-Dibenzyloxycarbonyl-L-lysyl-L-proline p-nitroanilide)

L-Proline p-nitroanilide hydrobromide (9.5 g, 0.03 mole) and $N^\alpha$, $N^\epsilon$- dibenzyloxycarbonyl-L-lysine (12.4 g, 0.03 mole) were coupled and the reaction mixture was worked up as in Example 6. The final product was obtained as an amorphous solid.

Yield 15.8 g.

This product was confirmed to be homogeneous by thin-layer chromatography.

EXAMPLE 13

(L-Lysyl-L-proline p-nitroanilide ditosylate)

$N^\alpha$, $N^\epsilon$-Dibenzyloxycarbonyl-L-lysyl-L-proline p-nitroanilide (9.5 g, 0.015 mole) was treated with 26% anhydrous hydrogen bromide solution in acetic acid (35 ml) and the reaction mixture was worked up as in Example 2. Thus, L-lysyl-L-proline p-nitroanilide dihydrobromide was obtained.

Yield 7.8 g.

The hydrobromide was dissolved in 0.1 M acetic acid, the solution was passed through a column of Amberlite IR-400 (acetate form, 200 ml), which was washed with 0.1 M acetic acid. The eluate and washings were combined, and evaporated to a residue under reduced pressure. The residue was dissolved in ethanol with p-toluenesulfonic acid monohydrate (5.5 g, 0.02 mole). Concentration of the solution under reduced pressure gave a residue which was crystallized by the trituration with ethyl ether.

Yield: 10.1 g
m.p.: 92°–130° C. (decomp.)
$[\alpha]_D^{25}$: −32.6° (C=1.1, water)

| Elemental Analysis | C | H | N% |
|---|---|---|---|
| Calcd. for $C_{31}H_{41}O_{10}N_5S_2 \cdot 2H_2O$: | 50.05 | 6.11 | 9.42 |
| Found: | 49.76 | 6.02 | 9.26 |

EXAMPLE 14

($N^\alpha$-Benzyloxycarbonyl-$N^{-G}$-tosyl-L-arginyl-L-proline p-nitroanilide)

L-Proline p-nitroanilide hydrobromide (12.0 g, 0.038 mole) and $N^\alpha$-benzyloxycarbonyl-$N^G$-tosyl-L-arginine, which was liberated from the cyclohexylamine salt (23.0 g, 0.041 mole), were dissolved in chloroform (60 ml), and 1-ethyl-3-(3-dimethylaminopropyl)-carbodiimide (6.8 ml, 0.038 mole) was stirred into the solution at 0° C. The mixture was stirred for additional 17 hours at room temperature, and it was worked up as in Example 3.

Yield 22.3 g.

This product was confirmed to be homogeneous by thin-layer chromatography.

EXAMPLE 15

(L-Arginyl-L-proline p-nitroanilide ditosylate)

$N^\alpha$-Benzyloxycarbonyl-$N^G$-tosyl-L-arginyl-L-proline p-nitroanilide (8.2 g, 0.012 mole) was treated with anhydrous hydrogen fluoride as in Example 9. After removal of excess hydrogen fluoride the residue was worked up as in Example 13. The final product was obtained as crystals.

Yield: 7.3 g
m.p.: 125°–138° C. (decomp.)
$[\alpha]_D^{25}$: −31.4° (C=1.0, water)

| Elemental Analysis | C | H | N% |
|---|---|---|---|
| Calcd. for $C_{31}H_{41}O_{10}N_7S_2 \cdot 5/2\ H_2O$: | 47.67 | 5.95 | 12.56 |
| Found: | 47.79 | 5.83 | 12.53 |

EXAMPLE 16

(N-Benzyloxycarbonyl-L-proline p-phenylazoanilide)

p-Phenylazoaniline (7.9 g, 0.04 mole) and N-benzyloxycarbonyl-L-proline (10.0 g, 0.04 mole) were coupled and the reaction mixture was worked up as in Example 6. Thus, the product was obtained as solid.

Yield 10.8 g.

The product was used in the following Example 17 without further purification. An analytical sample was prepared by recrystallizaton from n-hexane-ethyl acetate.

m.p.: 141°–143° C.
$[\alpha]_D^{20}$: −87.0° (C=1.0, dimethylformamide)

| Elemental Analysis | C | H | N% |
|---|---|---|---|
| Calcd. for $C_{25}H_{24}O_3N_4$: | 70.07 | 5.65 | 13.08 |
| Found: | 70.27 | 5.61 | 12.93 |

EXAMPLE 17

(N-t-Butyloxycarbonyl-glycyl-L-proline p-phenylazoanilide)

N-Benzyloxycarbonyl-L-proline p-phenylazoanilide (4.3 g, 0.01 mole) was treated with 25% anhydrous hydrogen bromide solution in acetic acid (35 ml) and the reaction mixture was worked up as in Example 2.

The L-proline p-phenylazoanilide hydrobromide thus obtained and t-butyloxycarbonylglycine (2.5 g, 0.014 mole) were coupled as in Example 6. The crude product thus obtained was purified by column chromatography, and the final product was obtained as crystals.

Yield: 3.4 g
m.p.: 172°–176° C.
$[\alpha]_D^{20}$: −110.1° (C=1.0, dimethylformamide)

| Elemental Analysis | C | H | N% |
|---|---|---|---|
| Calcd. for $C_{24}H_{29}O_4N_5$: | 63.84 | 6.47 | 15.51 |
| Found: | 64.08 | 6.73 | 15.18 |

EXAMPLE 18

(Glycyl-L-proline p-phenylazoanilide tosylate)

t-Butyloxycarbonyl-glycyl-L-proline p-phenylazoanilide (2.5 g, 0.0055 mole) was dissolved in acetic acid (8 ml) together with p-toluenesulfonic acid monohydrate (2.3 g, 0.012 mole), and the mixture was stirred at room temperature for 2 hours. The product was precipitated by adding ethyl ether to the reaction mixture, recovered by filtration, and washed with ethyl ether. The solid obtained was recrystallized twice from ethanol-ethyl ether.

Yield: 1.6 g
m.p.: 141°–155° C. (decomp.)
$[\alpha]_D^{20}$: −68.7° (C=1.0, dimethylformamide)
$\epsilon_{max}^{344}$: 25,000 (0.1N hydrochloric acid)

| Elemental Analysis | C | H | N% |
|---|---|---|---|
| Calcd. for $C_{26}H_{29}O_5N_5S \cdot H_2O$: | 57.65 | 5.77 | 12.93 |
| Found: | 57.53 | 5.60 | 12.99 |

Example 19

(N-Benzyloxycarbonyl-L-proline 4-phenylazo-1-naphthylamide)

4-Phenylazo-1-naphthylamine (4.9 g, 0.02 mole) and N-benzyloxylcarbonyl-L-proline (5.0 g, 0.02 mole) were coupled and the reaction mixture was worked up as in Example 6. The final product was obtained as crystals.

Yield: 3.5 g
m.p.: 136°–138° C.
$[\alpha]_D^{20}$: −75.9° (C=1.0, dimethylformamide)

| Elemental Analysis | C | H | N% |
|---|---|---|---|
| Calcd. for $C_{29}H_{26}O_3N_4$: | 72.78 | 5.48 | 11.71 |
| Found: | 72.68 | 5.57 | 11.93 |

EXAMPLE 20

(t-Butyloxycarbonyl-glycyl-L-proline 4-phenylazo-1-naphthylamide)

N-Benzyloxycarbonyl-L-proline 4-phenylazo-1-naphthylamide (2.5 g, 0.0052 mole) was treated with 25% anhydrous hydrogen bromide solution in acetic acid (25 ml) and the reaction mixture was worked up as in Example 2.

The L-proline 4-phenylazo-1-naphthylamide hydrobromide thus obtained and t-buthyloxycarbonyl-glycine (1.36 g, 0.0077 mole) were coupled by N, N'dicyclohexylcarbodiimide and the reaction mixture was worked up as in Example 6. The crude product was then purified by column chromatography, and the final product was obtained as crystals.

Yield 1.1 g.

This material showed single spot on thin-layer chromatography.

EXAMPLE 21

(Glycyl-L-proline 4-phenylazo-1-naphthyl amide)

t-Butyloxy-glycyl-L-proline 4-phenylazo-1-naphtylamide (1.0 g, 0.002 mole) was treated with p-toluenesulfonic acid monohydrate (0.76 g, 0.004 mole), and the reaction mixture was worked up as in Example 18. The glycyl-L-proline 4-phenylazo-1-naphthylamide tosylate thus obtained was dissolved in methanol, and neutralized with 5% sodium hydrogen carbonate solution to precipitate the product. The precipitate was were removed by filtration, washed with water, dried, and recrystallized from methanol-water.

Yield: 0.67 g
m.p.: 127°–138° C. (decomp.)
$[\alpha]_D^{20}$: −87.7° (C=1.0, dimethylformamide)
$\epsilon_{max}^{376}$: 14,400 (0.1 N-hydrochloric acid)

| Elemental Analysis | C | H | N% |
|---|---|---|---|
| Calcd. for $C_{23}H_{23}O_2N_5 \cdot 3/4\ H_2O$: | 66.56 | 5.95 | 16.88 |
| Found: | 66.45 | 5.81 | 16.69 |

EXAMPLE 22

The relation between the incubation time and the amount of substrate hydrohyzed was examined, glycyl-L-proline p-nitroanilide and human serum being used as substrate and enzyme source, respectively, and the assay of the substrate hydrolyzed was carried out by the following direct photometric method.

Glycyl-L-proline p-nitroanilide tosylate was dissolved in 2% non-ionic detergent (Nikkol NP-10; Nikko Chemicals, Osaka, Japan) aqueous solution in a concentration of 3 mM to prepare the substrate solution. The following four tubes were prepared:

(1) The experimental tube contained 0.5 ml of 0.15 M glycine-NaOH buffer (pH 8.7), 0.5 ml of the substrate solution, and 0.05 ml of human serum (2) The blank tube contained 0.5 ml of the 0.15 M glycine-NaOH buffer, 0.5 ml of the substrate solution and 0.05 ml of water.

(3) The standard tube contained 0.5 ml of the buffer, 0.5 ml of the substrate and 0.05 ml of 3 mM p-nitroaniline aqueous solution.

(4) The control tube contained 0.5 ml of the buffer and 0.5 ml of the substrate.

All tubes were incubated at 37° C. for the periods listed in Table 1, and the reaction was stopped by the addition of 3.0 ml of 1 M acetate buffer (pH 4.2) to every tube. To the control tube, 0.05 ml of the human serum was added after stopping the reaction. A photometer was adjusted to zero with the blank, and the absorbances of the experimental (E), control (C), and standard (S) were read at 385 nm in a cuvette with 1 cm light path. p-Nitroaniline liberated by the enzyme reaction was calculated by the equation $$E - C/S \times 150 \, (n \text{ mole})$$

The results are summarized in Table 1.

Table 1

| Incubation time (min) | Amount of p-nitroaniline formed (n mole) |
| --- | --- |
| 15 | 18.11 |
| 30 | 35.43 |
| 60 | 71.65 |
| 90 | 100.79 |
| 120 | 135.43 |

In accordance with the above data, it was confirmed that the enzyme reaction is linear with time.

The same procedure was repeated, a homogeneous enzyme preparation purified from human submaxillary gland being used instead of the human serum. As a result, the same relation was also confirmed.

EXAMPLE 23

The relation between the amount of enzyme and the amount of substrate hydrolyzed was examined, glycyl-L-proline p-nitroanilide tosylate and human serum being used as substrate and enzyme source, respectively, and the assay of the substrate hydrolyzed being carried out by the following azo-coupling method.

The following tubes were prepared:

(1) The experimental tube contained 1.0 ml of 0.15 M glycine-NaOH buffer (pH 8.7), 1.0 ml of the substrate solution prepared in Example 22, and the volume listed in table 2 of human serum.

(2) The control tube contained 1.0 ml of the glycine-NaOh buffer, and 1.0 ml of the substrate solution.

Both experimental and control tubes were incubated at 37° C. for 30 minutes, and 0.1 ml of the serum was added to the control tube. The reaction was stopped by adding 0.4 ml of 30% perchloric acid aqueous solution. After centrifuging at 3000 rpm for 10 minutes, each 0.5 ml of the supernatant was transferred to another tube; besides 0.1 ml of 0.5 m p-nitroaniline aqueous solution and 2.4 ml of 30% perchloric acid solution were added to the standard tube, and 2.5 ml of the perchloric acid solution was added to the blank tube.

To all the four tubes, 0.5 ml of 0.2% sodium nitrite aqueous solution at 4° C., and they were kept at 4° C. for 10 minutes. Then, 0.5 ml of freshly prepared 0.5% ammonium sulfamate aqueous solution was added. After 2 minutes, 1.0 ml of 0.05% N-(1-naphthyl) ethylenediamine solution was added and the mixtures were incubated at 37° C. for 30 minutes in the dark.

A photometer was adjusted to zero with the blank, and the absorbances of the experimental (E), control (C), and standard (S) were read at 548 nm.

p-Nitroaniline formed enzymically was calculated by the equation:

$$\frac{(E - C) \times 500 \, A}{S} \times \frac{2.5}{0.5}$$

(wherein, A is the volume of 0.5 mM p-nitroaniline aqueous solution used in the standard tube (ml)).

The results are summarized in Table 2.

Table 2

| Volume of serum (ml) | Amount of p-nitroaniline formed (n-mole) |
| --- | --- |
| 0.01 | 14.24 |
| 0.02 | 32.91 |
| 0.03 | 45.89 |
| 0.04 | 62.50 |
| 0.05 | 82.44 |
| 0.10 | 155.06 |

In accordance with the above data, it was confirmed that the enzyme reaction is linear with the amount of enzyme.

EXAMPLE 24

3 mM substrate solutions were prepared as in Example 22, various dipeptide derivatives or salts thereof being used as substrates. The relative enzyme activities toward various substrates, and the rates and optimum pHs of hydrolysis of various substrates with the enzyme were measured as in Example 21.

The results are summarized in Table 3.

Table 3

| Substrate | Optimum pH[a] | Km(M)[b] pH 7.0 | Relative enzyme activity (%)[c] | | |
| --- | --- | --- | --- | --- | --- |
| | | | Human serum pH 7.0 | Human serum pH 8.7 | Purified human submaxillary enzyme[d] pH 7.0 |
| L-lysyl-L-proline p-nitroanilide | 8.5 – 8.7 | $1.2 \times 10^{-4}$ | 122 | 71 | 121 |
| L-arginyle-L-proline[e] p-nitroanilide | 7.8 – 8.0 | $2.3 \times 10^{-4}$ | 86 | 55 | 94 |
| glycyl-L-proline | | | | | |

Table 3-continued

| | | | Relative enzyme activity (%)[c] | | |
|---|---|---|---|---|---|
| Substrate | Optimum pH[a] | Km(M)[b] pH 7.0 | Human serum pH 7.0 | Human serum pH 8.7 | Purified human submaxillary enzyme[d] pH 7.0 |
| p-nitroanilide L-alanyl-L-proline[f] | 8.5 – 8.7 | $3.3 \times 10^{-4}$ | 100 | 100 | 100 |
| p-nitroanilide L-glutamyl-L-proline | 8.5 – 8.7 | $1.4 \times 10^{-5}$ | 83 | 75 | 86 |
| p-nitroanilide L-aspartyl-L-proline | 8.5 – 8.7 | $2.3 \times 10^{-5}$ | 54 | 37 | 58 |
| p-nitroanilide | 8.5 – 8.7 | $8.1 \times 10^{-5}$ | 34 | 28 | 37 |

[a] Activities were measured in 0.15 M Tris-maleate buffer at pH 5.6 – 8.8 and in 0.15 M glycine-NaOH buffer at pH 8.2 – 9.4, purified human submaxillary enzyme being used. For L-alanyl-L-proline p-nitroanilide, amidiol buffer was used instead of glycine buffer, since glycine buffer interfered the photometry at pH 9 – 10.
[b] Km values were measured at 7.0 in Tris-maleate buffer, purified human submaxillary enzyme being used. The values are the meanof duplicate experiments.
[c] Activities were measured at pH 8.7 in 0.15 M Tris-maleate buffer or at pH in 0.15 M glycine-NaOH buffer. The valuesare the mean of duplicate experiments.
[d] The purified enzyme was obtained by the following method; The enzyme was solubilized from the microsomal fraction by autodigestion, and subsequently purified by $(NH_4)_2SO_4$ fractionation followed by Sephadex G-200 chromatography.
[e] The substrate was used as the ditosylate.
[f] The substrate was used as the hydrochloride.

EXAMPLE 25

The products obtained after incubating various X-L-proline p-nitroanilides with purified human submaxillary enzyme or human serum for 30 minutes as in Example 22 were examined by paper chromatography, the residues of glycine, L-alanine, L-glutamic acid, L-aspartic acid, L-lysine and L-argine being used as the N-terminal amino acids (X).

When the purified enzyme was used, only X-L-proline and p-nitroaniline in addition to the substrates were identified on the chromatogram, and X-OH, L-proline or L-proline p-nitroanilide was not observed.

When human serum was used as enzyme source with glycylproline p-nitroanilide as substrate, glycyl-L-proline, glycine, L-proline and p-nitroaniline were identified, but no L-proline p-nitroanilide was observed. When the rate of hydrolysis of L-proline p-nitroanilide by human serum was examined, it was observed only 0.7% of hydrolysis of glycyl-L-proline p-nitroanilide. Glycyl-L-proline was proved to be hydrolyzed to glycine and L-proline by human serum. These results indicate that glycyl-L-proline may be hydrolyzed preferentially by the X-prolyl dipeptidylaminopeptidase in human serum first to produce p-nitroanilide and glycyl-L-proline which is further hydrolyzed to glycine and L-proline by another enzyme in human serum.

EXAMPLE 26

3 mM of substrate solutions were prepared as in Example 22, glycyl-L-proline p-phenylazoanilide tosylate and glycyl-L-proline 4-phenylazo-1-naphthylamide being used as substrates.

The assay of enzyme activity was carried out by adding 0.05 ml of human serum to a mixture of 0.5 ml 1.5 mM glycine-NaOH buffer (pH 8.7) and 0.5 ml substrate solution in the experimental tube, incubating the resulting solution at 37° C. for 30 minutes, and then stopping the reaction with 3.0 ml 1N-hydrochloric acid. The absorbances were A 493 nm = 0.18 for glycyl-L-proline p-phenylazoanilide and A 532 nm = 0.80 for glycyl-L-proline 4-phenylazo-1-naphthylamide. These values are comparable to that for glycyl-L-proline p-nitroanilide.

EXAMPLE 27

The rate of hydrolysis of glycyl-L-proline p-phenylazoanilide was measured as in Example 26, human serum being used as enzyme. However, the blank tube contained water instead of the enzyme solution in the experimental tube, and the standard tube contained 3 mM p-phenylazo-aniline solution instead of the enzyme solution in the experimental tube.

As a result, the rate was 18.7 $n$ mole/min./1 serum.

EXAMPLE 28

The activity of x-prolyl dipeptidyl-aminopeptidase was measured as in Example 22, glycyl-L-proline p-nitroanilide and 88 normal human sera being used as substrate and enzyme, respectively.

The results are summarized in Table 4.

Table 4

| Group | No. subjects | Age (years) | Enzyme activity ($\mu$ mole/min/1 serum) average ± S. E. |
|---|---|---|---|
| Total | 88 | 15 – 81 | 54.88 ± 1.50 |
| Male | 53 | 15 – 81 | 56.30 ± 1.90 |
| Female | 35 | 20 – 76 | 52.49 ± 2.47 |
| Younger | 42 | 15 – 40 | 54.76 ± 2.07 |
| Male | 24 | 15 – 40 | 60.10 ± 2.84[a] |
| Female | 18 | 20 – 40 | 47.59 ± 2.07 |
| Older | 46 | 41 – 81 | 55.04 ± 2.23 |
| Male | 29 | 41 – 81 | 53.18 ± 2.43 |
| Female | 17 | 48 – 76 | 58.16 ± 4.37[b] |

[a] The value of younger males (not older than 40 years old) was significantly higher than that of younger females, $p < 0.001$.
[b] The value of older females was significantly higher than that of younger females, $p < 0.05$.

EXAMPLE 28

The activity of X-prolyl dipeptidyl-aminopeptidase was measured as in Example 22, glycyl-L-proline p-nitroanilide and 88 normal human sera from patients being used as substrate and enzyme sources, respectively.

The results are summarized in Table 5.

Table 5

| Group | Number of Cases | Enzyme activity ($\mu$ mole/min/1 serum) | Difference from control |
|---|---|---|---|
| Normal (control) | 88 | 54.9 ± 1.5 | — |
| Hepatitis | 23 | 75.8 ± 28.5 | $p < 0.01$ |
| Early essential hypertension | 20 | 80.94 ± 3.87 | $p < 0.001$ |
| Fixed essential hypertension | 17 | 89.29 ± 3.69 | $p < 0.001$ |
| Gastric Cancer | 37 | 38.4 ± 2.3 | $p < 0.001$ |
| Pulmonary Cancer | 17 | 39.8 ± 2.6 | $p < 0.001$ |
| Acute lymphocytic leukemia | 22 | 38.8 ± 11.9 | $p < 0.01$ |
| Lymphosarcoma | 11 | 36.3 ± 5.6 | $p < 0.01$ |

Table 5-continued

| Group | Number of Cases | Enzyme activity (μ mole/min/ 1 serum) | Difference from control |
|---|---|---|---|
| Hodgkin's disease | 15 | 31.0 ± 9.5 | p < 0.01 |

EXAMPLE 30

The activity of X-prolyl dipeptidyl-aminopeptidase was measured as in Example 22, various X-L-prolyl p-nitroanilides, and human sera from patients being used as substrates and enzyme sources, respectively.

The results are summarized in Table 6.

Table 6

| Group | No. of Cases | Enzyme activity (μ mole/min/1 serum ± S.E.) | | | | | |
|---|---|---|---|---|---|---|---|
| | | Gly | L-Ala | L-Asp | L-Glu | L-Lys | L-Arg[a] |
| Normal (control) | 3 | 50.4 ± 15.0 | 36.6 ± 9.6 | 37.7 ± 9.0 | 27.5 ± 7.5 | 18.2 ± 4.7 | 13.8 ± 3.6 |
| Hepatitis | 3 | 143.0 ± 31.8 | 99.5 ± 17.0 | 102.5 ± 17.5 | 74.8 ± 17.6 | 49.7 ± 10.2 | 35.5 ± 6.8 |
| Gastric Cancer | 3 | 25.3 ± 3.0 | 18.5 ± 1.9 | 17.6 ± 1.6 | 13.9 ± 1.3 | 8.2 ± 0.8 | 6.0 ± 0.7 |

[a]The terms, Gly, L-Ala, L-Asp, L-Glu, L-Lys and L-Arg in Table show the residue X of X-L-proline p-nitroanilide.

EXAMPLE 31

0.23 mg of crystalline glycyl-L-proline p-nitroanilide tosylate was dissolved in 100 ml water with stirring. It took ca. 30 minutes at 20° C. and ca.18 minutes at 30° C. for perfect dissolution.

On the other hand, 0.23 mg of porous glycyl-L-proline p-nitroanilide tosylate, which was prepared by freezing 15 m. mole aqueous solution of the same at −40° C. and then drying the freezed solid at 0.05 mmHg, was dissolved in 100 ml water with stirring as in the above procedure. It only took ca. 10 seconds at 20° C. and ca. 5 seconds at 30° C. for perfect dissolution.

What is claimed is:

1. Dipeptide derivatives having the structure:

X-L-proline-Y wherein X is a residue of an amino acid selected from the group consisting of glycine, alanine, valine, leucine, serine, threonine, phenylalanine, tyrosine, tryptophane, glutamic acid, aspartic acid, lysine and arginine; and Y is a residue of a compound selected from the group consisting of p-nitroaniline, p-phenylazoaniline, and 4-phenylazo-1-naphthylamine; and acid salts of said dipeptide derivatives.

2. Compounds as set forth in claim 1, wherein said X is a residue of glycine, alanine, glutamic acid, aspartic acid, lysine or arginine and said acid is p-toluenesulfonic acid, hydrochloric acid or hydrobromic acid.

3. Compounds as set forth in claim 2, wherein said Y is p-nitroaniline residue, and the sterochemical configuration of said X is the L form, with the exception that X is glycine residue.

4. Glycyl-L-proline p-nitroanilide.
5. Glycyl-L-proline p-nitroanilide tosylate.
6. L-lysyl-L-proline p-nitroanilide.
7. L-arginyl-L-proline p-nitroanilide.
8. L-alanyl-L-proline p-nitroanilide.
9. L-glutamyl-L-proline p-nitroanilide.
10. L-aspartyl-L-proline p-nitroanilide.

* * * * *